US00PP12458P2

(12) United States Plant Patent
Matsukizono

(10) Patent No.: US PP12,458 P2
(45) Date of Patent: Mar. 12, 2002

(54) PORTULACA PLANT NAMED 'SUMMER JOY LIGHT PINK'

(75) Inventor: Hiromi Matsukizono, Irisa (JP)

(73) Assignee: Sakata Seed Corporation (JP)

( * ) Notice: Subject to any disclaimer, the term of this patent is extended or adjusted under 35 U.S.C. 154(b) by 0 days.

(21) Appl. No.: 09/353,043

(22) Filed: Jul. 13, 1999

(51) Int. Cl.[7] ..... A01H 5/00
(52) U.S. Cl. ..... Plt./263
(58) Field of Search ..... Plt./263

(56) References Cited

U.S. PATENT DOCUMENTS

PP11,349 P * 4/2000 Babikow ..... Plt./263

OTHER PUBLICATIONS

UPOV ROM GTITM Computer Database 2000/04, GTI JOUVE Retrieval Software, citation for 'Summer Joy Light Pink', Aug. 2000.*

* cited by examiner

*Primary Examiner*—Bruce R. Campell
*Assistant Examiner*—Wendy C Baker
(74) *Attorney, Agent, or Firm*—Rothwell, Figg, Ernst & Manbeck

(57) ABSTRACT

Portulaca 'Summer Joy Light Pink' is a new variety of *Portulaca oleracea*. This plant has a vigorous, spreading plant growth which produces large, light pink flowers having a pale greenish-yellow center.

1 Drawing Sheet

BACKGROUND OF THE NEW PLANT

This invention relates to a new and distinct cultivar of Portulaca plant, hereinafter referred to by the name 'Summer Joy Light Pink'. Portulaca 'Summer Joy Light Pink' is a new variety of *Portulaca oleracea*. The plant has a vigorous spreading growth habit and can be used as a groundcover. It can also be used in a potted or hanging basket presentation. The invention's flowers are light pink (RHS 69A) with a pale greenish-yellow (RHS 1C) center. The flowers are single and measure 5.4 to 5.8 centimeters in diameter when fully open. There are five distinct petals with an indent at the tip of each petal. Portulaca flowers will typically close under low light and low temperature conditions such as late in the day and at night. 'Summer Joy Light Pink' Portulaca flowers will stay open later into the evening than most other cultivated varieties. The plant performs well in hot and dry climates. The plant is very resistant to rain, heat and drought.

ORIGIN AND ASEXUAL REPRODUCTION

The new cultivar is propagated asexually from vegetative cuttings. The asexual reproduction establishes that the plant does in fact maintain the characteristics described in successive generations. 'Summer Joy Light Pink' has been reproduced by stem cuttings in Salinas, Calif., and all of the characteristics thereof have been determined to be firmly fixed.

In June, 1994, a mutation line arose from 'Summer Joy Pink', which is currently pending in the U.S. Patent Office with Ser. No. 09/353,044, that possessed flowers that were a lighter shade of pink. This plant line was isolated and vegetatively reproduced for several more generations. In February, 1997, cuttings of this plant line were sent to California. During the spring and summer of 1997 and 1998, plants were grown under the direction and supervision of the inventor for evaluation of the stability of the line's desired traits. Plants were evaluated in greenhouse pots at the research station at Salinas, Calif., and at the breeding station in Kakegawa, Japan. The invention, 'Summer Joy Light Pink' Portulaca, was determined by the inventor to have its characteristics, as herein described, firmly fixed.

BRIEF DESCRIPTION OF DRAWINGS

The accompanying drawings serve by color photographic means to illustrate the new plant variety, 'Summer Joy Light Pink'. The colors are represented as true as possible using conventional photographic procedures.

DETAILED DESCRIPTION OF THE NEW VARIETY

Figure 1:
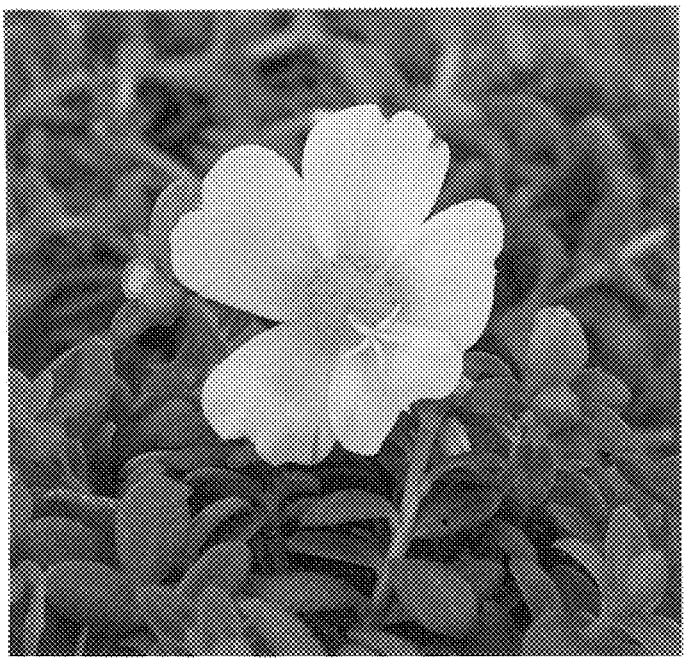
FIG. 1 is a close-up view of a 'Summer Joy Light Pink' flower illustrating its color and shape.
Figure 2:
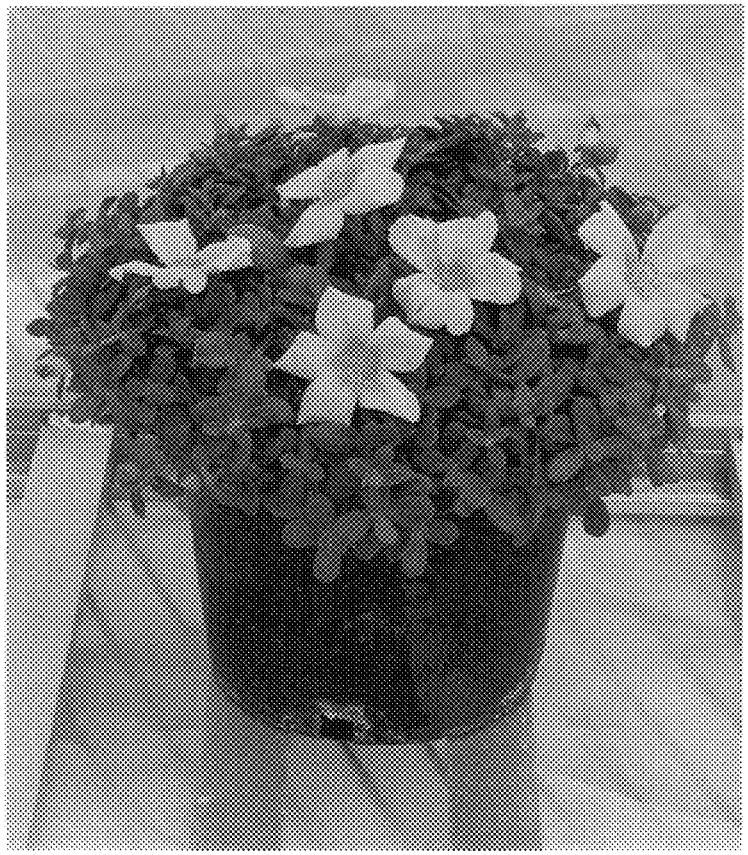
FIG. 2 is a view of the new cultivar after growing in a greenhouse for 8 to 10 weeks in a six-inch diameter pot.

The following description is based on observations and measurements from 14–16 week old plants grown in six-inch pots at Salinas, Calif. These plants were grown in plastic pots containing a peat moss-based medium. The plants were grown in the greenhouse under full sunlight in Salinas, Calif. Night temperatures ranged from 16° C. to 21° C. and day temperatures ranged from 24° C. to 35° C. The soil was not allowed to stay saturated but the plants were irrigated when the soil began to dry, or every second or third day. Soluble fertilizer was applied through an overhead irrigation system. The fertilizer contained 18% nitrogen, 8% phosphorus and 18% potassium. Every fourth irrigation was done with non-fertilizer water. Color designations were made according to The Royal Horticultural Society Colour Chart published by The Royal Horticultural Society of London, England.

Origin: Japan.

Parent: Sport of Summer Joy Pink (pending U.S. Patent application Ser. No. 09/353,044).

Classification:

*Family.*—Portulacaceae.

*Genus.*—Portulaca.

*Species.*—*Oleracea.*

*Commercial.*—Portulaca/Purslane 'Summer Joy Light Pink'.

Plant:

*Growth habit.*—Prostrate.

*Plant height.*—7 cm.

*Spreading area of plant.*—60–80 cm (in a six-inch pot).

*Vigor.*—The plant is most vigorous at high temepratures.

*Time to initiate/develop roots.*—Vegetative cuttings root in 7–10 days after placing into a rooting medium such as a peat moss-based mixture. The cuttings will form roots without the use of overhead mist.

Stem:

*Thickness.*—2.2 mm.

*Color.*—Yellowish green (144C) with red-purple RHS 60A anthocyanin pigment present in the axial portion of the stem.

*Pubescence.*—Present only at the nodes.

*Branching.*—Abundant.

*Length of internode.*—10–20 mm.

Leaf:

*Shape.*—Oblanceolate with cuspidate tip in mature leaves and acute tips in younger leaves near the apex of the stem.

*Length* (*average*).—2.1 cm.

*Width* (*average*).—1.0 cm.

*Thickness.*—1.5 mm.

*Color.*—Upper leaf surface is green RHS 137A and the lower surface is green (137C).

*Pubescence.*—None.

*Texture.*—Leaf surface is smooth, shiny and wax-like. Leaves are thick and fleshy.

Flower:

*Shape.*—Five distinct petals with an indent at tip of petal.

*Petal shape.*—Heart-shaped with a square base; approximately 1.7×1.4 cm.

*Lobation.*—None.

*Diameter.*—5.4–5.8 cm when fully opened.

*Color.*—Unopened stage (the development stage at which the petals have elongated from the sepals but not yet fully extended and opened): Light pink (68D); Upper petal color is red-purple (69A); Lower petal color is red-purple (69B); Mature stage: Light pink (69A), with a yellow-green (154A) center.

*Bud.*—Lanceolate shaped; mature bud measures 1.6 cm in length and 0.7 cm in diameter; color is yellow-green (145A).

*Sepal.*—Two sepals, deltoid shaped; measures 1 cm in length and 0.9 cm in width; sepals are thin, paper-like, smooth and shiny; color is transparent with green venation.

*Habit.*—The flowers bloom during midmorning and close at night. Each flower blooms only once and are produced throughout the growing season. The plants produce flowers regardless of day length; the plants are day neutral. Plants can have 40 to 50 open flowers at one time and have no fragrance.

*Season of bloom.*—In zone 9 and similar locations this plant will flower throughout the entire year. Growth is less vigorous during the cool temperatures and short days of winter, but the plant will continue to bloom.

*Hardiness.*—Plant is heat tolerant; thrives in heat and humidity; plant is not cold tolerant or below 7° C.

*Reproductive organs.*—One yellow (4C) pistil with five narrow style branches and many yellow (4C) stamen with yellow (4C) anthers and filaments. Stigma is white. Pollen is orange (26A); does not produce seed.

Disease and Insect Resistance

No unusual susceptibility to diseases or insects have been observed.

Comparison with Other Know Varieties

The new variety is distinguished from other Portulaca plants known to inventor by its flower color, larger flower size and ability to stay open later into the evening. The closest commercial cultivar that we are aware of is the Portulaca plant named 'Yubi® Light Pink' (an unpatented variety). The distinguishing characteristics, which differentiate 'Summer Joy Light Pink' from 'Yubi® Light Pink', are:

| | 'Summer Joy Light Pink' | 'Yubi ® Light Pink' |
|---|---|---|
| Flower Diameter | 5.4–5.8 cm | 4.3–4.8 cm |
| Flower Color | Solid light pink with pale greenish-yellow center | Light pink with white streaks at edges and tip |
| Flower Closing Behavior | Open longer in evening | Closes earlier in afternoon |

We claim:

1. A new and distinct cultivar of Portulaca as shown and described herein.

* * * * *